(12) United States Patent
Browne (10) Patent No.: US 9,345,828 B2
(45) Date of Patent: May 24, 2016

(54) SAFETY BAG SPIKE INTERFACE FOR HAZARDOUS DRUGS

(75) Inventor: Thomas Anthony Browne, Colorado Springs, CO (US)

(73) Assignee: Thomas Anthony Browne, Colorado Springs, CO (US)

( * ) Notice: Subject to any disclaimer, the term of this patent is extended or adjusted under 35 U.S.C. 154(b) by 731 days.

(21) Appl. No.: 13/135,157

(22) Filed: Jun. 27, 2011

(65) Prior Publication Data

US 2012/0330246 A1    Dec. 27, 2012

(51) Int. Cl.
*A61M 5/14*     (2006.01)
*A61M 5/162*    (2006.01)
*A61M 39/10*    (2006.01)
*A61M 39/26*    (2006.01)
*A61M 39/00*    (2006.01)

(52) U.S. Cl.
CPC ............. *A61M 5/1407* (2013.01); *A61M 5/162* (2013.01); *A61M 5/1408* (2013.01); *A61M 39/10* (2013.01); *A61M 39/26* (2013.01); *A61M 2039/0009* (2013.01); *A61M 2039/0027* (2013.01); *A61M 2039/1077* (2013.01)

(58) Field of Classification Search
CPC .. A61M 5/1407; A61M 5/1408; A61M 5/162
USPC ............ 604/80, 81, 244, 245, 246, 247, 256, 604/257, 258, 262, 533, 534, 535, 537, 538, 604/905
See application file for complete search history.

(56) References Cited

U.S. PATENT DOCUMENTS

| | | | | |
|---|---|---|---|---|
| 4,392,851 | A * | 7/1983 | Elias | A61J 1/2089 604/244 |
| 6,447,498 | B1 * | 9/2002 | Jepson et al. | 604/411 |
| 7,815,614 | B2 | 10/2010 | Fangrow | |
| 2007/0282278 | A1 * | 12/2007 | Knight | 604/236 |
| 2008/0103487 | A1 * | 5/2008 | Miyasaka | 604/537 |
| 2009/0008393 | A1 * | 1/2009 | Howlett et al. | 220/380 |
| 2011/0034899 | A1 * | 2/2011 | Thome et al. | 604/407 |

* cited by examiner

*Primary Examiner* — Kevin C Sirmons
*Assistant Examiner* — Shefali Patel (57) ABSTRACT

A convenience kit, use of which transforms a conventional IV container spiking and dispensing system to a safety system for handling hazardous drugs. The kit provides a spike receiving subsystem which is interposed between a spike of an IV set and a needle-less syringe connector affixed to a hazardous drug containing IV container to provide a closed pathway for delivering the hazardous drugs and to allow for detaching a spent container without exposing the hazardous drugs to a surrounding environment.

7 Claims, 8 Drawing Sheets

SAFETY BAG SPIKE INTERFACE FOR HAZARDOUS DRUGS

FIELD OF INVENTION

This invention generally relates to apparatus and methods for making and using medical convenience kits and, more specifically, for making convenience kits which have a specific purpose of providing closed system sequential accessing of hazardous solutions being dispensed from an IV container used in patient drug delivery and especially for drug delivery using medicines which present a hazard if exposed to an open environment.

BACKGROUND AND DESCRIPTION OF RELATED ART

Philosophically and practically, a medical device, such as that embodying Applicant's invention, to be truly useful in modern contemporary practice must not only be considered safe and efficient, but must also be cost effective. There are many facets of related devices which affect cost effectivity. For examples, many medical devices in common use have wide distribution resulting in low-cost, high volume manufacturing and large numbers of clinicians trained for their use, leading to a high standard of safety and efficacy.

A wide variety of IV solutions are delivered from IV containers (e.g. bags and bottles). Commonly, for such use, a conventional IV set is provided with a proximally disposed spike for accessing a medical solution within an IV container. It is common also that, when a container is emptied, the spike may be removed from the last used container and used to spike a subsequent container.

However, when hazardous drugs are being so dispensed, a closed connection system should be employed to assure complete containment of all hazardous drug especially when a disconnection is effected. If there is no such connection system, an entire IV set would have to be thrown away when an IV container is emptied. If the delivery path is directly through an inserted patient catheter, cost of disposal of the set may be compounded by inconvenience and perhaps an unwarranted painful experience to a patient as the used IV set and catheter are replaced.

Also, as a safety precaution, IV containers containing hazardous drugs are commonly delivered pre-spiked to a site of use. Also commonly, the spiked access pathways are closed by a needle-less syringe connector. While it is known in the IV dispensing art to use a needle-less syringe connector and an associated male luer drip-less connector to provide a closed, but separable connection for a specific IV delivery system as exemplified in FIG. 1C of U.S. Pat. No. 7,815,614 B2 issued Oct. 19, 2010 to Thomas F. Fangrow, Jr., et al. (Fangrow), it is considered costly and, therefore, inappropriate to saddle all IV container deliveries with the cost of IV sets having specialized connectors when such is not required for a large portion of drug dispensing.

It is for this reason that it is appropriate to interpose a detachable male luer drip-less connector between a spike of an associated conventional IV set and a needle-less syringe connector. Such an interposition provides a closed connection for the IV set spike and a drip-less male luer connector which is readily affixed and detached with safety to the needle-less syringe to provide for exchanging a spent IV container for one, subsequently attached thereto while maintaining a closed system. It is for such a critical and important purpose this instant invention is provided. While it is an object of Fangrow to provide a closed disconnection, the device disclosed in Fangrow cannot provide service for an IV set having a proximal spike.

TERMS AND DEFINITIONS

In the following table 1 is a list of terms and associated definitions provided to improve clarity and understanding of precepts of the instant invention:

closed system, n: a system, the contents of which are kept disparate from the surrounding environment convenience kit, n: a medical device kit as defined by the United States FDA disparate, adj: totally separate drip-less connector, n: a fitting associated with a needle-less connector, designed to provide an open connection when affixed to a needle-less connector and to provide a closed luer fitting when detached therefrom fluid, n: a gas or liquid.

HD, n: hazardous drug.

IV set, n: intravenous drug delivery tubing specifically dedicated for use with an associated IV catheter and IV container.

IV bag, n: a container, generally made of plastic in the form of a bag used to hold IV fluids containing medications for delivery through an IV set IV bottle, n: a container generally made from glass and used to hold IV medications for delivery through an IV set kit, n: a group of parts, provided within a single package for a designated medical use luer fitting, n: a medical connector which is in common use in medical practice.

luer locking connector, n: a connector associated with a luer fitting having a locking mechanism whereby a male and female connector are securely, but generally releasibly affixed one to the other.

needle-less syringe connector, n: a fitting which permits needle free fluid access to an IV set or through a vial adapter and which has interface geometry similar to a conventional syringe.

subassembly, n: a part of an assembly.

subsystem, n: a part of a system.

unitized, adj: joined e.g. a plurality of separate parts permanently adhered together to become a single unit.

BRIEF SUMMARY AND OBJECTS OF THE INVENTION

In brief summary, this novel invention alleviates all of the known problems related to providing a detachable connector which is interposed between a needle-less syringe connector, affixed to an IV container which is used to delivery hazardous drug, and an IV set having a proximally disposed IV container spike. It being duly noted that a detachable connector for such use must provide a closed system before and after being disconnected.

The instant invention is referenced herein as a spike receiving subsystem. This subsystem has a drip-less male luer connector on a proximally disposed end (towards a needle-less syringe connector which is affixed to an IV container spike, referenced herein as a spiking subsystem). As disclosed supra, an IV container containing hazardous drug is generally delivered to a site of use, pre-spiked with a spiking subsystem (i.e spike affixed needle-less syringe connector) to provide a closed delivery pathway from the IV container.

On a distal end, the spike receiving subsystem has an elongated hollow tube affixed thereto, providing an enclosed, proximally directed pathway to the drip-less connector. The hollow tube is sized and of sufficient length to seize an inserted IV container spike and thereby provide a closed pathway which terminates at the proximally disposed drip-less male luer connector.

Thus, when an IV container spike is inserted into the tube and the drip-less male luer connector is affixed to a spiking subsystem which is further joined to an IV container, a closed pathway from IV set to the IV container is engendered. When the spike receiving subsystem is disconnected from the spiking subsystem, the common connecting sites are each closed by the male luer drip-less connector and needle-less syringe connector, respectively, to provide a safety disconnect and opportunity to replace the used and spent IV container with safety.

It is therefore a primary object to provide a convenience kit hazardous drug transfer device which provides for opening a fluid delivery pathway from an IV container which is a source of hazardous drug to an associated IV set fitted with a conventional IV container spike.

It is a further object to provide a pathway from an associated IV container to an IV set, the pathway being kept disparate from the surrounding environment.

It is an object to provide a spike receiving subsystem which is compatible with a spiking subsystem associated with an IV set used with an IV bag.

It is another object to provide a spike receiving subsystem which is compatible with a spiking subsystem associated with an IV set used with an IV bottle.

It is yet another object to provide a spike receiving subsystem wherein the drip-less male luer connector and the elongated hollow spike receiving and engaging tube are joined by a secure bond thereby providing a unitized spike receiving subsystem convenience kit.

These and other objects and features of the present invention will be apparent from the detailed description taken with reference to accompanying drawings.

DETAILED DESCRIPTION OF THE ILLUSTRATED EMBODIMENT

In this description, the term "proximal" indicates the segment of the device normally closest to the object of the sentence describing its position. The term distal refers to a segment oppositely disposed. Reference is now made to the embodiments illustrated in FIGS. 1-11 wherein like numerals are used to designate like parts throughout. For parts which are similar but not the same as parts originally specified with a given number, a prime of the original numbers is used. It is important that all parts selected for use in convenience kits associated with the instant invention, be able to be sterilized, for example, by such methods as gamma radiation.

Figure 1:
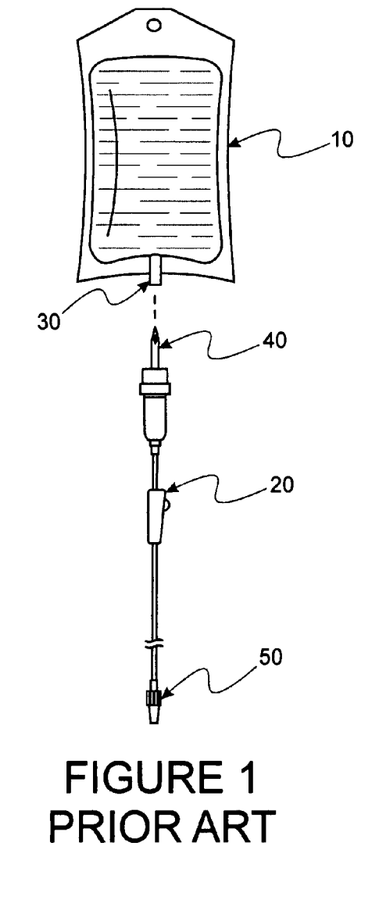
FIG. 1 is a frontal elevation of a PRIOR ART IV bag and an associated PRIOR ART IV set with an IV bag spike on a proximal end thereof.
Figure 2:
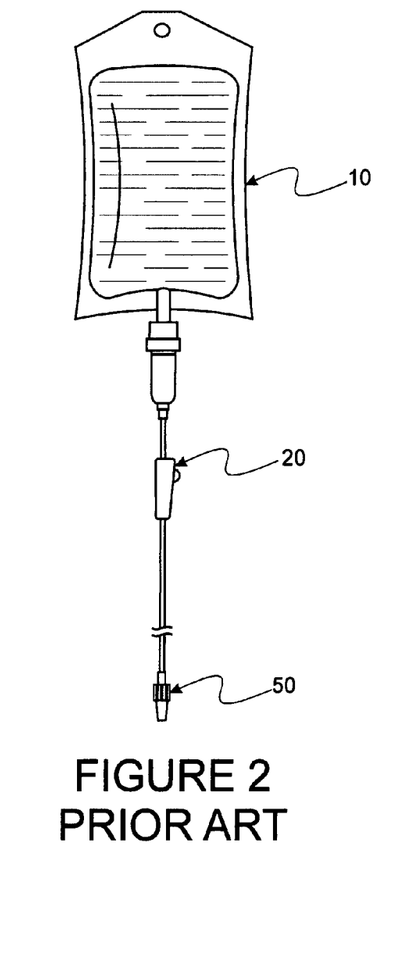
FIG. 2 is a frontal elevation of the PRIOR ART parts seen in FIG. 1 joined to spike the IV bag.

An exemplary IV container (i.e. an IV bag 10) and an illustrative IV container spiking set 20 are seen in FIG. 1. Both IV bag 10 and IV container spiking set 20 are available, in many forms, as contemporary conventional medical devices. Bag 10 has a spike receiving portal 30. Set 20 is equipped with a proximally disposed spike 40 which is sized and shaped to be inserted into and thereby be securely affixed to bag 10 through portal 30. Set 20 is seen so affixed to bag 10 in FIG. 2. Generally, IV 20 set is fitted with a fitting 50 by which set 20 may be further connected to a patient line (catheter) or a primary IV line, not seen in FIGS. 1-3, but seen in FIG. 4.

Figure 4:
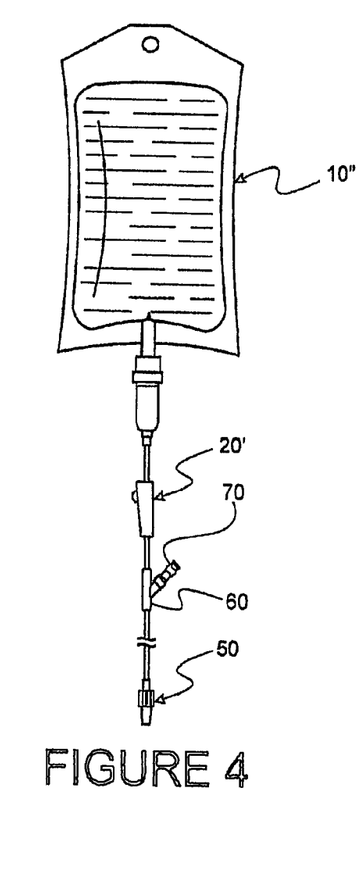
FIG. 4 is a frontal elevation of a primary IV set and an associated IV bag.

It is common practice to provide a primary IV container 10" and associated primary IV set 20', examples of which are seen in FIG. 4. A "Y" site 60 of IV set 20' provides an entry attachment port usually fitted with a needle-less syringe connector 70. Use of connector 70 is disclosed in detail hereafter. A distally disposed fitting 50 may be provided for connecting to a patient line (e.g. a catheter).

Figure 3:
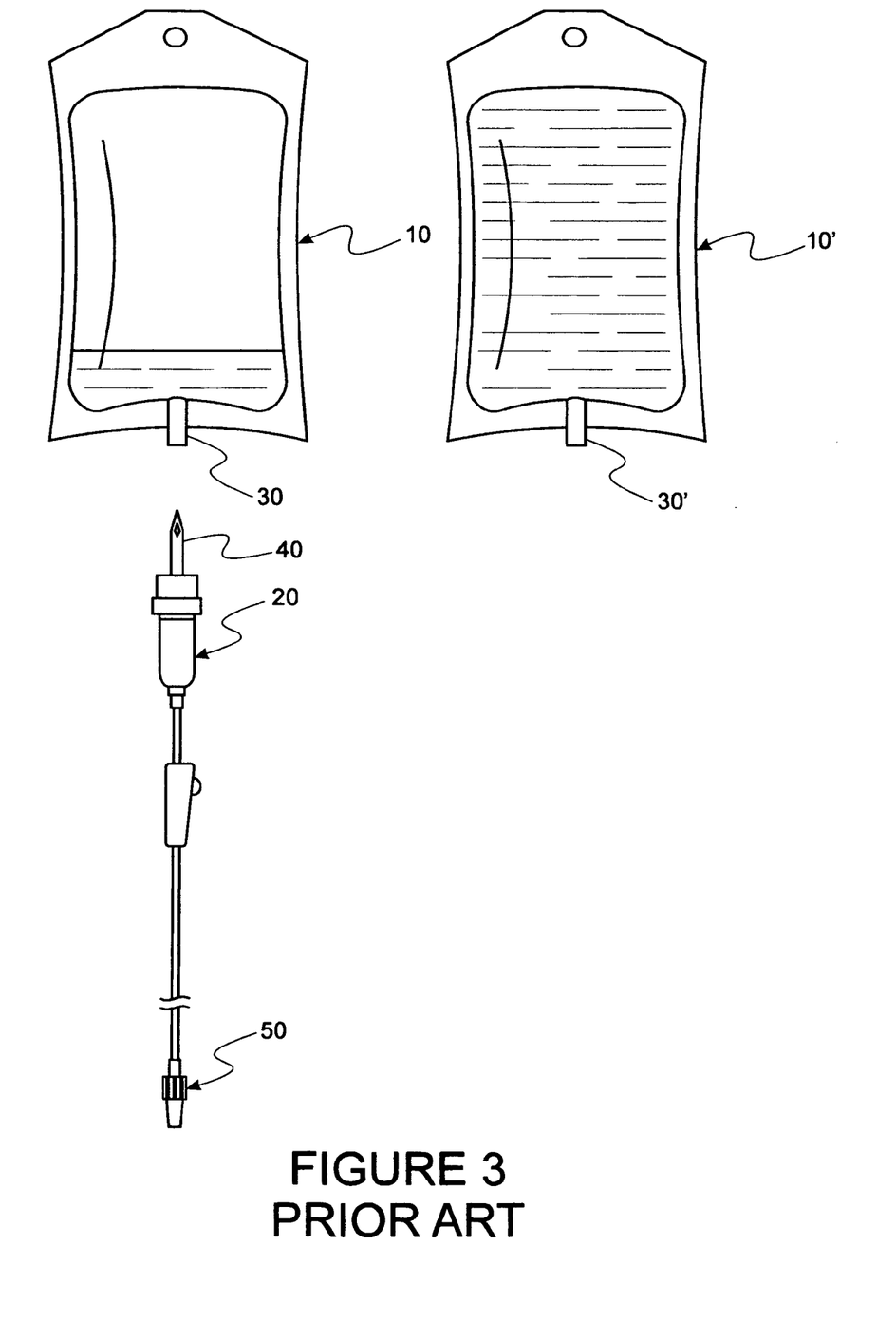
FIG. 3 is a frontal elevation of the PRIOR ART IV set seen in FIG. 1 uncoupled from a spent IV bag with a second IV bag disposed for subsequent use.

It is also common practice for a spike 40 to be removed from portal 30 when contents of bag 10 are depleted, as seen in FIG. 3. Spike 40 may then be inserted into a second portal 30' of an IV bag 10' for continuing drug delivery via a second IV solution source. While such may be acceptable, using careful practices, for some delivered drugs, such is not the case for hazardous drugs. Removing spike 40 from portal 30 provides two sources of contamination to the external environment, leakage at portal 30 and residue on spike 40 and leakage therefrom.

To provide opportunity to remove an IV container, of which IV bag 10 is an example, for replacement by another IV container, of which bag 10' is an example (see FIG. 3) when dispensing hazardous drugs, a delivery system must be provided with a delivery system which does not expose hazardous drug to the surrounding environment. Even so, it is desired to use devices and parts, such as those seen in FIGS. 1-3, which are part of available conventional facility inventory.

Figure 5:
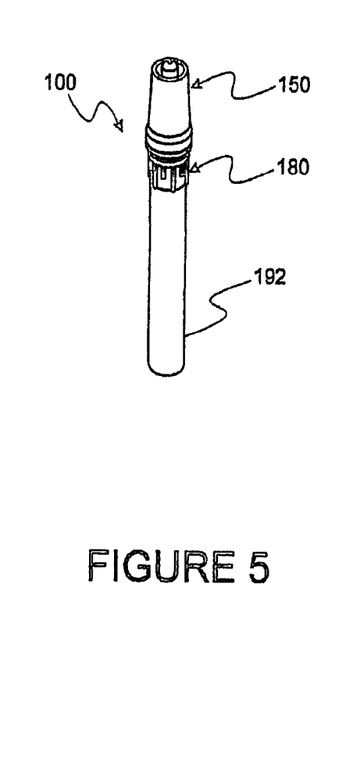
FIG. 5 is a perspective of an exemplary spike receiving subsystem, according to the present invention.
Figure 6:
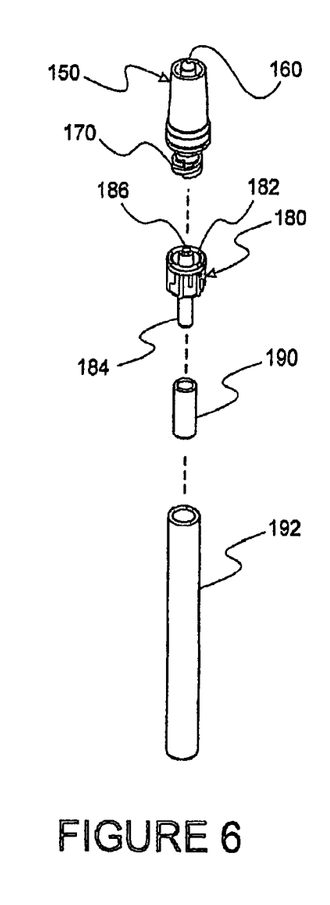
FIG. 6 is an exploded view of the spike receiving subsystem seen in FIG. 5.
Figure 7:
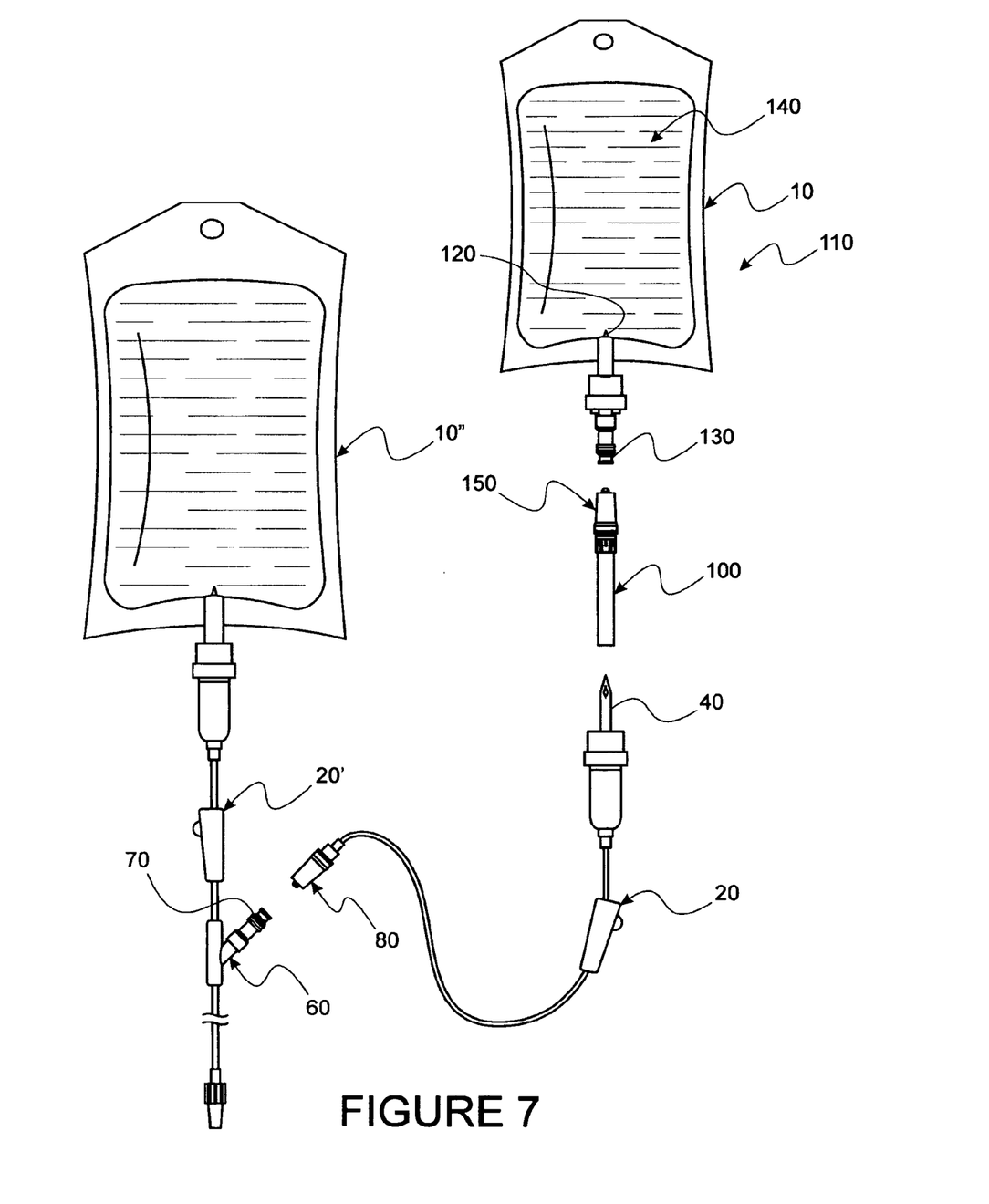
FIG. 7 is a pre-assembled view of the primary IV set and associated IV bag seen in FIG. 4, an IV set with a spike on a proximal end, the spike receiving subsystem seen in FIG. 5 and a spiking subsystem affixed to an IV bag which contains a hazardous medication.

Reference is now made to FIGS. 5-10, wherein the instant invention and associated conventional parts are seen. As seen in FIG. 7, drug delivered in an IV bag 10 may be dispensed through a primary set 20' which is ultimately affixed to a patient line distally (not shown).

As seen in FIG. 7, a spike receiving subsystem 100 is interposed between an IV set 20 and a pre-filled IV bag subsystem 110 comprising an IV bag 10 spiked by a bag spike 120 affixed to a needle-less syringe connector 130. Generally, spiking of an IV bag 10 containing hazardous drug (generally depicted by the number 140, herein) is performed in safety enhanced facilities by well trained pharmacists. IV bags (such as IV bag 10) are filled with hazardous drug 140 and kept disparate from surrounding environment by closure associated with a needle-less connector 130 affixed to the bag via spike 120, usually prior to filling.

Before opening a pathway from IV bag 10, a connection should be made between spike 40 and spike receiving subsystem 100. Spike receiving subsystem 100 is better seen in FIGS. 5 and 6. As seen in FIG. 6, spike receiving subsystem comprises a drip-less male luer connector 150. Connector 150 has a proximally disposed male luer fitting 160 which is compatible with a needle-less syringe connector and a valve which opens when affixed to a needle-less syringe connector and which closes when detached therefrom. On the end distal to fitting 160, connector 150 has a female luer lock fitting 170.

Figure 8:
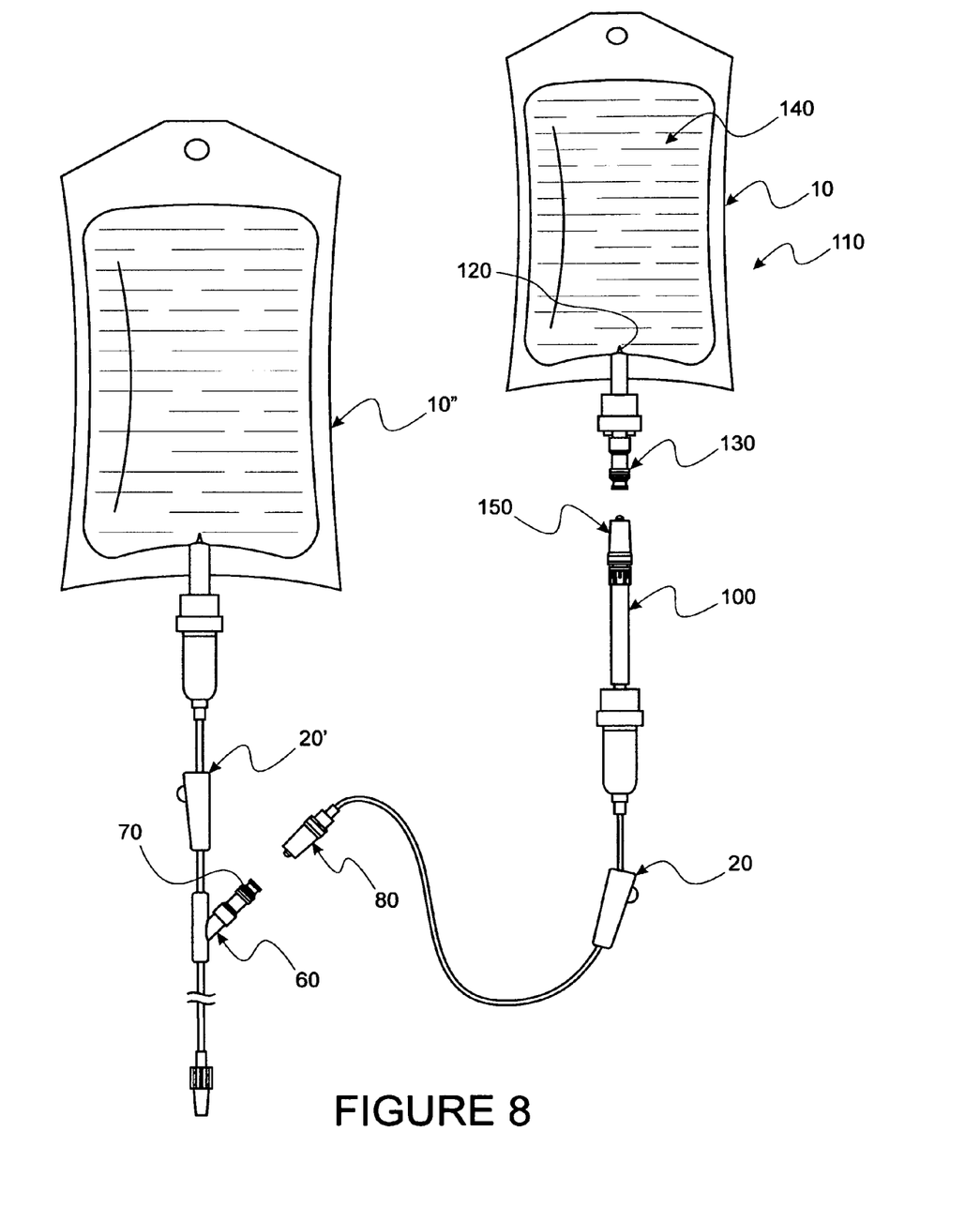
FIG. 8 is a frontal elevation of the parts seen in FIG. 7 with the spike on the porixmal end inserted into the spike receiving subsystem.

Further, subsystem 100 comprises a male luer fitting 180, having a male luer lock fitting 182 which is securely affixed (preferably unitized) to female luer lock fitting 170. On an end distal to fitting 192, fitting 180 comprises a hollow stub 184 providing a communicating through hole 186 to fitting 182. A hollow cylindrical tube 190 is provided as a spacer whereby an elongated hollow tube 192 is affixed to stub 184 and fitting 180. Tube 190 is sized and shaped to accept and seize upon an inserted spike 40 to provide a secure, leak-free communicating interface. An assembled subsystem 100 is seen in FIG. 5. In FIG. 8, subsystem 100 is seen securely affixed to spike 40.

Tube 190 may be made from a length of Alpha 2222C-78 PVC tubing cut to a length consistent with seizing spike 40. Connector 150 may be a Texium® connector available from CareFusion Corporation.

Figure 9:
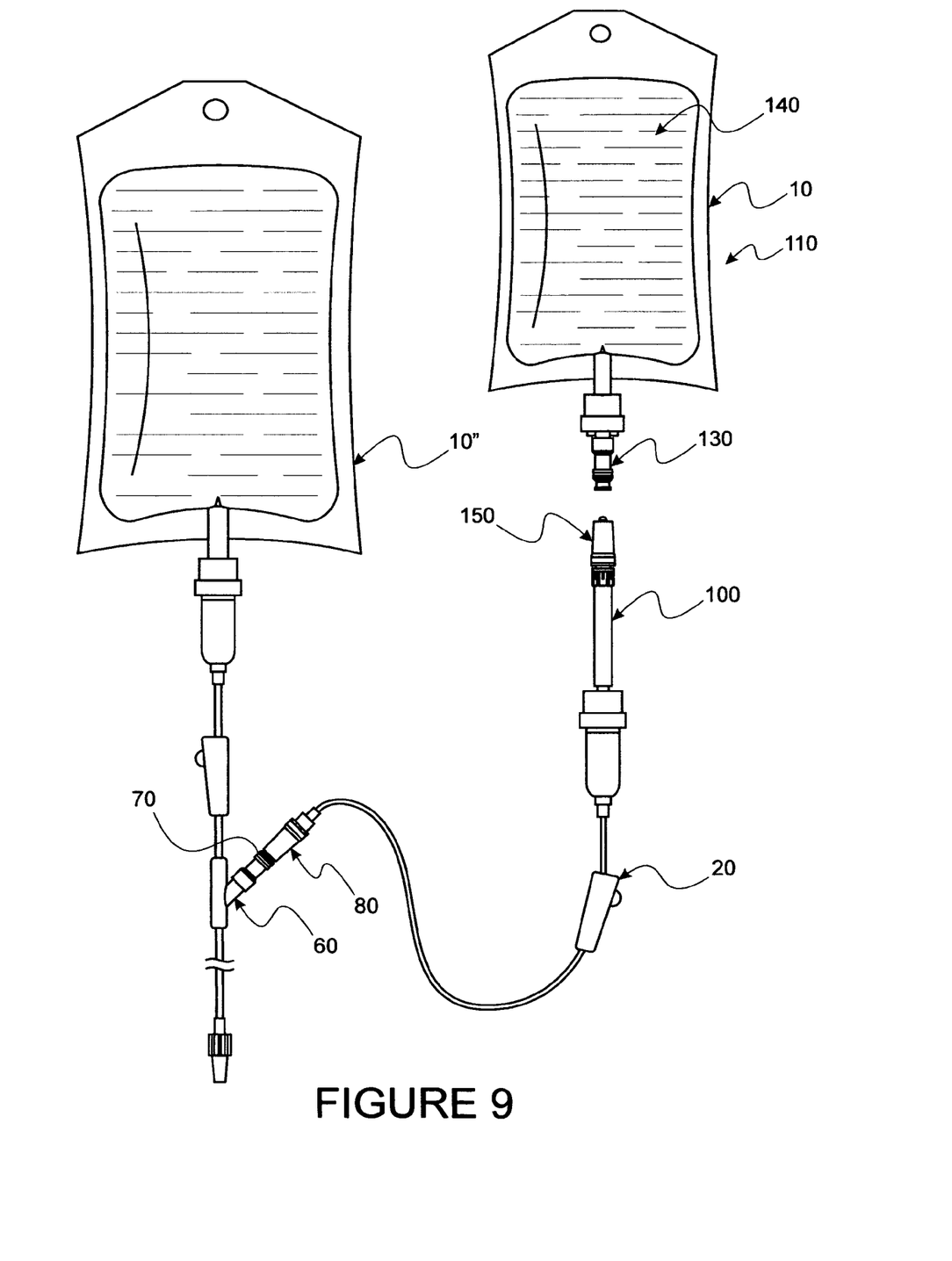
FIG. 9 is a frontal elevation of the parts seen in FIG. 8 with a distal male luer connector of the IV set with the spike on the proximal end affixed to the primary IV set.
Figure 10:
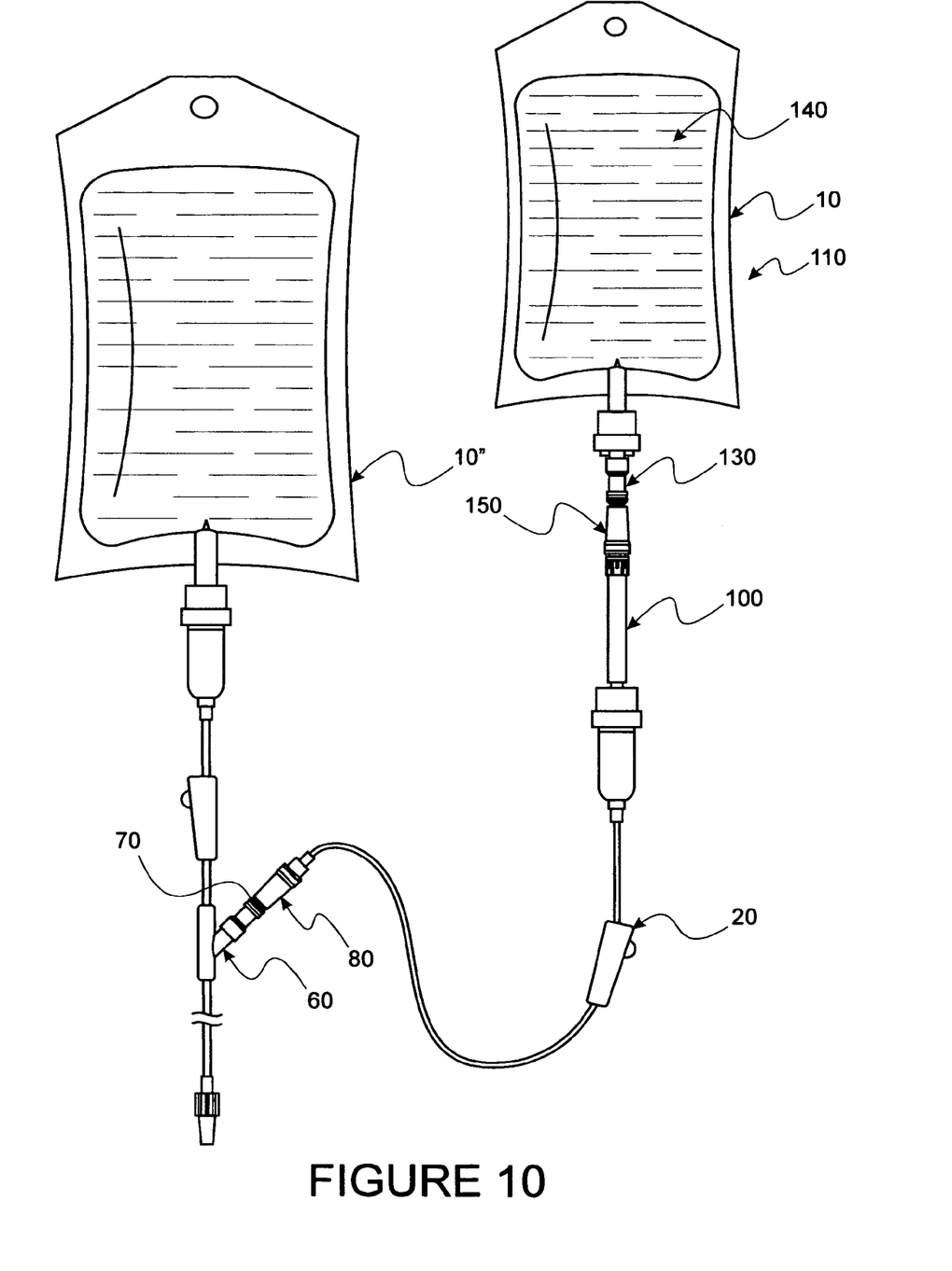
FIG. 10 is a frontal elevation of the parts seen in FIG. 9 joined to form a closed pathway from the IV bag through the spike receiving subsystem to the primary IV set.
Figure 11:
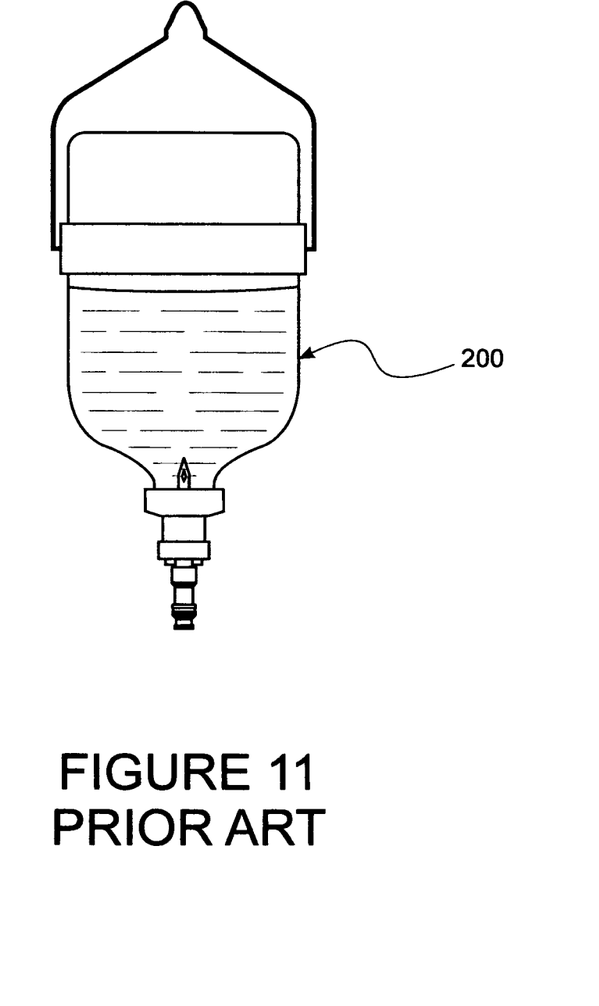
FIG. 11 is a frontal elevation of a PRIOR ART glass bottle IV container.

Also before opening the pathway from IV bag 10, a connection should be made between distally disposed fitting 80 and connector 70, as seen in FIG. 9. Finally, connection is made between needle-less connector 130 and drip-less male luer connector 150 to provide a pathway for commencing dispensing of drug 140. See FIG. 10. Note that when drug 140 in IV bag 10 is spent, connector 130 may be disconnected from connector 150 as valves within each connector close to provide a safety disconnection for replacing spent IV bags.

While IV bag 10 is used as an exemplary IV container in the disclosure provided supra, other containers, accessible by spiking (with a spike such as spike 40), may also be viewed as being within the scope of the instant invention. Such a container may be an IV bottle 200, seen in FIG. 11.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A hazardous drug transfer system which provides for sequentially opening a fluid delivery pathway from each container selected from a plurality of IV containers, at least one of which is a source of a hazardous drug, to a single pathway in an associated IV set fitted with an IV container spike thereby providing a fluid delivery pathway which is disparate from a surrounding environment for dispensing a fluid from each container through the associated IV set when a luer fitting connection is implemented and for providing closure for each pathway when parted as each container is disconnected therefrom, such that the fluid associated with each container is kept disparate from the surrounding environment and the fluid associated with the IV set is also kept disparate from the surrounding environment when the luer fitting connection is disengaged and detached, said system comprising:

spiking subsystems comprising a spiking component for accessing each container, each one of said spiking components being securely affixed to a needle-less syringe connector fitting which comprises a female luer fitting which is opened by insertion of a male luer fitting and is self-closing when the male luer fitting is displaced therefrom;

a spike receiving subsystem comprising a dripless connector comprising the male luer fitting that is self-closing and which interfaces with said female luer fitting of said needle-less syringe connector fitting to provide the opened fluid delivery pathway when connected thereto, said receiving subsystem further comprising an elongated spike receiving and engaging tube securely affixed to the dripless connector by a fluid-tight interface on one end and open for fluid-tight insertion and retention of the container spike of the associated IV set on another end whereby each of the subsystems is connected with one another for common fluid communication and then separated to permit replacement of a previously used IV container by another IV container while keeping the fluid within the parted pathways disparate from the surrounding environment.

2. The hazardous drug transfer system according to claim 1 wherein said needle-less syringe connector fitting is a Smartsite® needle-less connector.

3. The hazardous drug transfer system according to claim 1 wherein said dripless connector is a self-closing Texium® male luer connector.

4. The hazardous drug transfer system according to claim 1 wherein said male luer fitting is a male luer lock fitting.

5. The hazardous drug transfer system according to claim 1 wherein each container is an IV bag.

6. The hazardous drug transfer system according to claim 1 wherein each container is an IV bottle.

7. The hazardous drug transfer system according to claim 1 wherein said dripless connector and said spike receiving and engaging tube comprise a common bonded interconnection thereby providing a unitized spike receiving subsystem convenience kit.

* * * * *